(12) United States Patent
Coleman et al.

(10) Patent No.: US 9,808,010 B2
(45) Date of Patent: Nov. 7, 2017

(54) CHEWABLE COMPOSITION

(71) Applicant: VIRBAC CORPORATION, Fort Worth, TX (US)

(72) Inventors: Dan Coleman, Wentzville, MO (US); Steve Standley, Hazelwood, MO (US)

(73) Assignee: VIRBAC CORPORATION, Fort Worth, TX (US)

( * ) Notice: Subject to any disclaimer, the term of this patent is extended or adjusted under 35 U.S.C. 154(b) by 15 days.

(21) Appl. No.: 14/791,996

(22) Filed: Jul. 6, 2015

(65) Prior Publication Data
US 2017/0006894 A1 Jan. 12, 2017

(51) Int. Cl.
| | | |
|---|---|---|
| *A61K 9/00* | (2006.01) | |
| *A61K 31/506* | (2006.01) | |
| *A61K 31/7048* | (2006.01) | |
| *A61K 47/10* | (2017.01) | |
| *A61K 47/26* | (2006.01) | |
| *A61K 47/38* | (2006.01) | |
| *A61K 47/44* | (2017.01) | |
| *A61K 47/46* | (2006.01) | |
| *A23K 20/105* | (2016.01) | |
| *A23K 20/121* | (2016.01) | |
| *A23K 20/158* | (2016.01) | |
| *A23K 20/163* | (2016.01) | |
| *A23K 50/42* | (2016.01) | |
| *A23L 27/26* | (2016.01) | |
| *A23L 27/30* | (2016.01) | |
| *A23L 29/00* | (2016.01) | |
| *A23L 29/30* | (2016.01) | |
| *A01N 43/90* | (2006.01) | |
| *A61K 31/4985* | (2006.01) | |
| *A23K 20/195* | (2016.01) | |
| *A23K 50/40* | (2016.01) | |
| *A61K 9/20* | (2006.01) | |
| *A61K 9/14* | (2006.01) | |

(52) U.S. Cl.
CPC ............ *A01N 43/90* (2013.01); *A23K 20/105* (2016.05); *A23K 20/121* (2016.05); *A23K 20/158* (2016.05); *A23K 20/163* (2016.05); *A23K 20/195* (2016.05); *A23K 50/40* (2016.05); *A23K 50/42* (2016.05); *A23L 27/26* (2016.08); *A23L 27/30* (2016.08); *A23L 29/03* (2016.08); *A23L 29/04* (2016.08); *A23L 29/30* (2016.08); *A61K 9/0056* (2013.01); *A61K 31/4985* (2013.01); *A61K 31/506* (2013.01); *A61K 31/7048* (2013.01); *A61K 47/10* (2013.01); *A61K 47/26* (2013.01); *A61K 47/38* (2013.01); *A61K 47/44* (2013.01); *A61K 47/46* (2013.01); *A23V 2002/00* (2013.01); *A61K 9/146* (2013.01); *A61K 9/2013* (2013.01); *A61K 9/2054* (2013.01)

(58) Field of Classification Search
CPC .. A61K 9/0056; A61K 9/2013; A61K 9/2018; A61K 9/2031; A61K 9/2054; A61K 9/2068; A61K 31/4985; A61K 31/506; A61K 31/7048; A61K 47/10; A61K 47/26; A61K 47/38; A61K 47/44; A61K 47/46; A23K 20/105; A23K 20/121; A23K 20/158; A23K 20/163; A23K 50/40; A23K 50/42; A23L 27/26; A23L 27/30; A23L 29/03; A23L 29/04; A23L 29/30; A23V 2002/00
See application file for complete search history.

(56) References Cited

U.S. PATENT DOCUMENTS

| | | | |
|---|---|---|---|
| 6,086,940 | A | 7/2000 | Axelrod |
| 6,387,381 | B2 | 5/2002 | Christensen |
| 7,914,816 | B2 | 3/2011 | Kalbe et al. |
| 7,955,632 | B2 | 6/2011 | Paulsen et al. |
| 8,541,019 | B2 | 9/2013 | Isele |
| 8,628,794 | B2 | 1/2014 | Isele |
| 2004/0037869 | A1 | 2/2004 | Cleverly et al. |
| 2004/0151759 | A1 | 8/2004 | Cleverly et al. |
| 2006/0141009 | A1 | 6/2006 | Huron et al. |
| 2006/0222684 | A1 | 10/2006 | Isele |
| 2007/0128251 | A1 | 6/2007 | Paulsen et al. |
| 2008/0075759 | A1 | 3/2008 | Paulsen et al. |
| 2008/0160067 | A1 | 7/2008 | Boeckh et al. |
| 2013/0197006 | A1 | 8/2013 | Kanikanti et al. |
| 2014/0094418 | A1 | 4/2014 | Isele |

FOREIGN PATENT DOCUMENTS

| | | |
|---|---|---|
| EP | 2063869 A2 | 6/2009 |
| WO | 02/00202 A1 | 1/2002 |
| WO | 2004/014143 A1 | 2/2004 |
| WO | 2004016252 A1 | 2/2004 |

(Continued)

OTHER PUBLICATIONS

International Search Report and Written Opinion dated Aug. 18, 2016 in corresponding international application No. PCT/US2016/040028 (11 pages) (US20040037869 corresponding to WO2004016252 (D2), US20040151759 (D3), WO2012049156 (D5) and corresponding US20130197006, WO2005013714 (D6).

*Primary Examiner* — John Pak
*Assistant Examiner* — Nathan W Schlientz
(74) *Attorney, Agent, or Firm* — Westerman, Hattori, Daniels & Adrian, LLP

(57) ABSTRACT

A chewable composition, comprising at least one pharmaceutically active ingredient component; solid components including at least one flavor, and at least one disintegrant including at least one non-starch disintegrant; flowable components including a flowable oil, and at least one wetting agent other than water.

25 Claims, No Drawings

(56) References Cited

FOREIGN PATENT DOCUMENTS

| WO | 2005/013714 A1 | 2/2005 | |
|---|---|---|---|
| WO | 2008030469 A2 | 3/2008 | |
| WO | 2012/049156 A1 | 4/2012 | |
| WO | WO 2013068371 A1 * | 5/2013 | ........... A61K 9/0056 |
| WO | 2014/141223 A1 | 9/2014 | |

* cited by examiner

CHEWABLE COMPOSITION

FIELD OF THE INVENTION

The present invention relates to a chewable composition, typically for presenting a pharmaceutical ingredient to an animal.

BACKGROUND ART

Administration of pharmaceutical agents to animals is often difficult because some administration modes are complex, such as injections, and others are typically not available or inconvenient, such as suppositories or tablets. It would be advantageous to administer a pharmaceutical agent to an animal orally, but animals are often reluctant especially when the ingredient has an unappealing taste.

Various articles have been proposed for oral administration.

WO0200202 proposed a starch-based article with a Shore A hardness of 10 to 100. In addition to the pharmaceutically active compound, the article includes a high amount of starch (45% cornstarch or 55% wheat flour in the examples), but a low amount of beef or liver aromas (10%), and bodying agents such as cellulose acetate powder. Humectants are glycerol and water, which are present in amounts of 5 and 15%, respectively.

WO2005013714 proposed a ductile chewable composition including, in addition to the active ingredient, a combination of meat flavoring and partially gelatinized starch, along with a softener such as glycerol, polyethylene glycol (PEG) or polypropylene glycol (PPG), and water. In the examples, the amount of meat flavor is about 30% (w/w), the amount of pre-gelatinized starch is about 30 to 40%, and glycerin and water are both present in amounts or 14 and 4%, respectively.

WO2014141223 proposed a chewable formulation that does not use water as a humectant. A disintegrant is present in some embodiments. In some examples, meat flavor up to 10% and/or sweetener are present. Some embodiments include a filler which is typically cellulose-based. A solid fat is used as a lubricant, and glycerin and/or PPG as plasticizers/humectants. None of the formulations includes a flowable oil.

SUMMARY OF THE INVENTION

An objective of the invention is to propose a chewable composition for oral presentation of a pharmaceutical agent to an animal, which is stable, accepted easily by the animal, and which promotes delivery of the active ingredient(s) after ingestion.

Another objective of the invention is to propose a chewable composition that avoids, minimizes or reduces added water as an ingredient.

Another objective of the invention is to obtain a composition of the desired consistency while avoiding, minimizing or reducing the use of fillers such as cellulose-based fillers.

Another objective of the invention is to facilitate manufacturing of the composition, for example, by an extrusion-based process.

In view of one or more of these objectives, in one aspect, the chewable composition of the present invention uses a wetting agent other than water, in combination with a non-miscible flowable oil. Surprisingly, it has been observed that this combination of flowable ingredients makes it possible to obtain a chew that is stable, has a desirable consistency, and/or is easy to manufacture and package.

In another aspect, flavors are based mainly on a meat flavor and dry ingredients include a non-starch disintegrant. An advantage of this feature is that a chew having a high content of meat flavor can be obtained that has an adequate cohesion but will be easily divided or even disintegrated at the time of administration.

In another aspect, the chewable composition of the present invention can be prepared with little or no added filler such as cellulose-, soy-, and silicone-based fillers, with little or no added water, and/or with little or no added surfactant or emulsifier.

DETAILED DESCRIPTION OF PARTICULAR EMBODIMENTS

More aspects and characteristics of the invention will appear by reading the following description of particular embodiments.

In the present application, unless indicated otherwise, percentages are given by weight (w/w) of the total, especially total weight of the composition. As used herein, "substantially" and "about" means an acceptable variation according to conventional standards, otherwise at most a 2% variation from an indicated effect or value.

According to one aspect, the present invention provides a chewable composition, comprising:
  at least one pharmaceutically active ingredient component;
  solid components including:
    at least one flavor;
    at least one disintegrant including at least one non-starch disintegrant
  flowable components including:
    a flowable oil;
    at least one wetting agent other than water.

Additional features present in some embodiments are as follows:
  The flavor includes a meat flavor.
  The flavor includes a meat powder.
  The flavor includes a meat flavor and a sweet flavor.
  The non-starch disintegrant is croscarmellose sodium.
  The flowable oil is a liquid oil.
  The wetting agent is glycerin.
  The flowable oil is a vegetable oil.
  The flowable oil is soybean oil.
  The wetting agent is glycerin and the flowable oil is soybean oil.

According to another aspect, the present invention provides a chewable composition, comprising:
  at least 25% of a flavor;
  at least 15% of a disintegrant including at least 10% of a non-starch disintegrant;
  at least 10% of a wetting agent other than water;
  at least 5% of a flowable oil.

Other features present in some embodiments, alone or in combinations of two or more, are as follows:
  The flavor includes at least 12% of a meat flavor.
  The flavor includes at least 10% of a sweet flavor.

According to another aspect, the present invention provides a chewable composition, comprising:
  at least 12% of a meat flavor;
  at least 10% of a non-starch disintegrant;
  at least 10% of a wetting agent other than water;
  at least 5% of a flowable oil.

Other features present in some embodiments, alone or in combinations of two or more, are as follows:

The chewable composition comprises:
from 15% to 25% of the meat flavor;
from 10% to 20% of the non-starch-based disintegrant;
from 10% to 20% of the wetting agent other than water;
from 5% to 15% of the flowable oil.

The chewable composition comprises from 5% to 15% of polyethylene glycol.

The chewable composition comprises from 5% to 15% of a sweet flavor.

The chewable composition comprises from 2% to 12% of starch-based filler.

The amount of the wetting agent and the flowable oil is from 15% to 35%.

The chewable composition contains less than 5% of cellulose-, soy- and silicone-based fillers.

The chewable composition contains less than 2% unbound water.

According to another aspect, the present invention provides a chewable composition, comprising:
from 0.01% to 10% of at least one pharmaceutically active ingredient;
from 25 to 35% of a flavor including at least 12% of a meat flavor and at least 10% of a sweet flavor;
from 5 to 12% of PEG, cocoa butter, a lipid emulsifier, or a mixture of two or more thereof;
from 10 to 20% of a non-starch disintegrant;
from 5 to 12% of a starch;
from 12 to 15% of glycerin, PPG, or a mixture thereof;
from 8 to 12% of a liquid oil.

Preferably, the chewable composition has bioequivalence with a corresponding tablet form. In some embodiments, the chew has higher tolerance and/or digestability by the animal, for example, due to the presence of the disintegrant and fluids.

In one embodiment, the composition provides complete disintegration in water within at most 1 hour (in particular for large-size chew), preferably at most 45 minutes (in particular for medium-size chew), even more preferably at most 35 minutes (in particular for small-size chew), for example, at most 25 minutes (in particular for toy-sized chew). Disintegration can be tested in water at room temperature. Complete disintegration means that the composition is reduced to a soft mass having no palpably firm core, and in particular, a slurry in which no observable larger particles of the composition remain, with preferably substantially no particles having a dimension of more than about 2 mm, even preferably no particles having a dimension of more than about 1 mm. Complete disintegration can also be evaluated according to the appropriate U.S. Pharmacopeia testing procedures.

Chewable means that the composition is malleable and/or ductile at room temperature. Accordingly, the composition is not totally hard and can be chewed, but without substantially crumbling when compressed. The composition is not totally elastic, although it may exhibit some springiness in at least some embodiments.

In particular embodiments, the composition is shelf-stable for at least 1 month, preferably at least 3 months, even more preferably at least 6, 12, 24 or even 36 months. Shelf-stable means that liquid does not substantially separate from the composition, but the composition preferably remains flexible, even more preferably with a shiny surface aspect and/or an absence of dryness marks on the surface of the chew. Shelf stability also refers to a non-significant variation, i.e. less than 5%, preferably less than 2%, preferably less than 1%, in actives principle content in the composition. Shelf-stability can be measured in a sealed container, for example.

In some embodiments, the chewable composition comprises substantially no cellulose-based filler such as cellulose powders, or substitutes, such as soy-based or silicone-based fillers or powders. Preferably, the chewable composition contains less than 5%, more preferably less than 2%, even more preferably no added cellulose-based filler or substitutes, or less than 5% of all cellulose-, soy- and silicone-based fillers, preferably less than 2%.

The composition includes solid ingredients and flowable ingredients. Solid ingredients may include powders, whereas flowable ingredients may include pourable cohesive fluids, such as slurries, wet ingredients and/or liquids, in particular, at room temperature, but not powders. Each solid and flowable component may include one or several ingredients. For example, the active ingredient component may include one or several active ingredients, for example. In the following description, the description or mention of an ingredient in the singular includes the description or mention of a plurality of this type of ingredient, and vice versa, unless indicated otherwise expressly or from the context.

Active Ingredient Component

The active ingredient component may be the active ingredient(s) alone in liquid or solid form. If in solid form, the active ingredient component may be the active ingredient(s) alone, for example, in powder form, or a particle or granule including the active ingredient(s), in pure form or as a granulation of the active ingredient with excipient(s) and formulation additive(s) forming a powder, which maintains its integrity at least substantially in the manufacture of the chewable composition.

For example, the active ingredient component may be in the form of a dispersed phase within a continuous matrix formed by a mixture or agglomeration of the other ingredients. In these or other embodiments, the active ingredient component is in the form of a core partially or totally surrounded by a coating formed by the mixture of the other ingredients. A granule may contain a single active ingredient, or a combination of several or all active ingredients.

The active ingredient includes, in some embodiments, at least one active agent capable of controlling ecto-parasites, endo-parasites, or bacterial or viral pathogens, or combinations thereof. The active ingredient can be any veterinary pharmaceutically acceptable agent proven to be useful in the prevention or treatment of animal diseases, such as pain management, stress management, nutraceutics, skin support, urinary support, dental support, joint support, behavioral support, heart health support, in particular heart failure, chronic kidney disease, for example.

The active ingredient is, for example, an anthelmintic, such as ivermectin, praziquantel, pyrantel or pyrantel derivative such as pyrantel pamoate, and combinations of some or all thereof. Other active agents can also be used in the framework of the present invention, such as antibiotics, cephalosporins, AINS, coxibs, diuretics, phenylpyrazoles, milbemycins, avermectins, neonicotinoids, insect growth regulators, isoxazolines, thiazolines and derivatives. The active agents can be selected from the non-limiting list consisting of: doxycycline, amoxyciline, clavulanic acid, quinolones, corticoids, prednisolone and prednisolone derivatives, pimobendan, torsemide, benazepril, nitempyram, lufenuron, pyriproxyfene, selamectin, afoxolaner, fluralaner, sarolaner, spinosad, imidacloprid, for example. The active ingredient is present in a pharmaceutically effective amount in the composition.

The active ingredient component is present typically in an amount of up to 15%, or up to 12%, up to 10%, even only up to 5% or 2%, or even 1%, or substantially such amounts. In some embodiments, the active ingredient alone is present in such proportions. An efficient amount of the active ingredient is, for example, at least 0.001%, or at least 0.01%, or at least 0.05%, or even at least 0.1%.

In the active ingredient component, the active ingredient can be present in an amount of up to 99.99%, for example, up to 90%, or from 0.01 to 85%.

For example, the active ingredient component may include a filler such as a cellulose-, soy- or silicone-based filler, for example microcrystalline cellulose, in an amount of up to 90%, such as from 10 to 90%, or 60 to 80%. A disintegrant may be present in the active ingredient component, for example, a non-starch disintegrant. The disintegrant when present may be in an amount of up to 90%, for example, 0.01 to 20%, or 8 to 20%, for example, about 15%.

The role of the disintegrant is to expand and break the particle or granule of the active ingredient component and make the active ingredient available in the gastro-intestinal tract after ingestion.

In particular embodiments, the active ingredient is present in an amount of ivermectin about 0.1% or 0.115%, pyrantel pamoate about 85% or 83.742%, praziquantel about 50% or 50.484%, or combinations of at least two thereof.

The active ingredient component preferably does not contain water. Preferably, the active ingredient component does not contain alcohol. Alternatively, the active ingredient component is substantially free of unbound water, substantially free of unevaporated alcohol, or both.

The active ingredient can be a nutritionally active or pharmaceutically active ingredient. In the present description, the term "pharmaceutical" includes "nutritional" and "nutraceutical," such as a vitamin, for example, unless indicated otherwise expressly or from the context. The active ingredient is intended for a human or a non-human animal, especially a non-human mammal, such as a dog and/or a cat.

In some embodiments, the active ingredient is formed into the active ingredient component before incorporation into the chewable composition. For example, the active ingredient is coated with one or several coatings, granulated, incorporated into particles, or a combination thereof. The formulation of the active ingredient(s) into the active ingredient component(s), separately or together, can be designed to stabilize the active ingredient or to mask taste or odors, for example.

Unless indicated otherwise expressly or from the context, the proportions and amounts of ingredients set forth in the description of the chewable composition do not include ingredients of a particle or granule forming the active ingredient component(s) including the active ingredient(s). However, in some embodiments, the proportions and amount of the ingredients as set forth herein include the ingredients contained in the active ingredient component(s).

Solid Ingredients

In addition to the active ingredient(s) when the active ingredient component is in solid form, the solid ingredients include at least one of the following: flavor, disintegrant, filler, sweetener, plasticizer, binder, preservative. Preferably, at least a flavor and a disintegrant are included, along with a plasticizer and/or a binder. For example, all of the above-listed ingredients are included along with the active ingredient(s). A single ingredient can play the role of several of the above-listed ingredients. For example, a flavor can be a sweet flavor and/or act as a filler, and a plasticizer can also act as a binder.

Solid form means that the ingredient is added in a non-liquid and non-flowable cohesive form. Typically, but not exclusively, solid forms are particles, granules and/or powders.

The composition can be obtained by extrusion, with compression, or, in some embodiments, substantially without compression. A compressible sugar can be used in some embodiments, alone or in combination with a non-compressible sugar. In particular, a non-compressible and/or granular form can be used or a mixture of granular and compressible forms.

Flavor Component

It is advantageous to include a high proportion of meat flavor in the composition in order to improve acceptance by carnivorous animals, especially dogs and cats.

An optional sweet flavor can also improve acceptance, by itself or by enhancing the meat flavor. A ratio of meat flavor to sweet flavor in the solid ingredients can be from 1:1 to 2:1, for example, or the flavor advantageously includes at least 60% meat flavor, or even at least 66% or 75%. The meat flavor is typically more than 10% of the total blend, i.e., notably, at least 12%, preferably at least 13%, more preferably at least 14%, even more preferably 15%, or even at least about 16, 17 or even at least about 18%. For example, the meat flavor is present in an amount of from 15 to 25%. The flavors, typically meat and sweet flavors, with optional additional flavors, are present, for example, in an amount of at least 25%, such as from 25 to 35%, or at most 30%.

Meat flavors can include meat aromas, meat extract, and meat powders, for example, beef or chicken liver powder. The meat flavor may be natural or artificial.

The sweet flavor can be, for example, a natural sweetener such as glucose, fructose, sucrose, lactose, dextrose, glycerol, sorbitol, xylitol, maltitol, lactitol, glycerol, or an artificial sweetener such as aspartame, saccharin, acesulfame, sodium cyclamate, or a combination of at least two thereof. For example, the sweet flavor may include granulated sucrose, powdered sucrose, or combinations thereof.

When a filler is used, advantageously, the filler includes at least 50% sweetener, preferably substantially all the filler (excluding starches) is made up of the sweetener.

The sweetener is present in an amount of, for example, at least 5%, or at least 8%, preferably at least 10%, even more preferably at least about 13%, for example, from 5 to 15%.

The ratio of flavor, as compared to the total solid ingredients, can be from 1:3 to 3:3, for example, or about 2:3, and as compared to the flowable ingredients, from 1:1 to 3:1, for example, or about 3:2.

Disintegrant Component

A proportion of 5 to 25% disintegrant can be useful in the chew, for example, about 15%, or at least about 15%. If the proportion of disintegrant is too low, there is a risk that the chew will not disintegrate easily after ingestion. If the proportion of disintegrant is too high, it is difficult to manufacture the chew and there is a risk that the structure of the chew will lack cohesion.

The proportion of disintegrant to the other inactive ingredients or fillers can be, for example, 1 to 50%, 10 to 30%, 15 to 25%, or combinations or portions of these ranges.

Among disintegrants, so-called super-disintegrants, especially croscarmellose sodium, are preferred. However, other disintegrants can be used, similar to those commonly used in conventional marketed products, such as tablets. The consistency of the chew can be adjusted by adjusting the amount of disintegrant, for example, a product that is less ductile and more like a hard compressed tablet may include less disintegrant.

When moisture is introduced to the disintegrant, the close proximity of the disintegrant molecules to other particles of the tablet causes an explosive expansion, allowing the chew to break apart and release the API(s) more readily. When the chew is extruded and not compressed, or extruded with a low compression ratio, there is more space between the aggregated and/or adhered particles of the product. To facilitate break-up of the product, more disintegrant is useful to fill these spaces and make contact with other particles of the chew.

In particular, for a product that has the consistency of a chewable block (e.g. a chew), the quantity of croscarmellose sodium is usually significantly higher than for a conventional tablet form. In an illustrative embodiment, an amount of 1% croscarmellose sodium was found to be unacceptable for performing disintegration using the tablet disintegration method, as the block did not fully disintegrate within the designated pull time.

In order for the chewable block to perform similarly to that of the tablet, the quantity of croscarmellose sodium is typically increased as compared to a tablet. Thus, in one embodiment, a medium chewable block containing 15% croscarmellose sodium had a disintegration profile closely similar to that of the similar medium tablet containing 1% croscarmellose sodium.

Preferably, a content of at least 10%, for example, 10 to 20% or even 12 to 20% of non-starch disintegrant, for example, croscarmellose sodium, is useful to promote acceptable disintegration as compared to the tablet having less than 5%, less than 2%, such as 1% or less, croscarmellose sodium.

In particular, a fast disintegration rate of the chew is preferable, since the animal may only partially chew the product and thus, large undivided portions of dosage may be ingested. A fast disintegrating chew allows for the large portions to disintegrate in the gastro-intestinal tract. The disintegrating rate can be measured using U.S. Pharmacopeia (USP) procedure, such as USP <701>, for example.

Starch Component

Starches are useful in at least some embodiments as binders and/or disintegrants. Depending on the desired consistency, starches can be pre-gelatinized, for example, partially or totally pre-gelatinized. Chemically modified starches are alternatives or supplements to pre-gelatinized starches. A limited amount of starches is complemented by disintegrant other than starches, for example, so-called super-disintegrant. The amount of disintegrant is adjusted to obtain adequate consistency as well as the desired breaking down of the chew after ingestion by the animal.

The starch filler has little or no effect on extrusion as long as the amount is low, preferably up to 12%, up to 10% or up to 8%. When the amount of starch is too high, the chew becomes dryer and more brittle. The starch can also act as a disintegrant. Advantageously, the starch(es) is/are present in an amount of at least 2%, at least 5%, or about 8%, for example, 2 to 12%, or 5 to 12%.

A partially pre-gelatinized starch is usually preferred to reach a desirable consistency and to provide additional disintegration capacity.

Plasticizer/Binder Component

In some embodiments, a plasticizer and/or binder is/are present, for example, in an amount of up to 15%, or up to 12%, or even up to 10%, for example, 5 to 15%, 2 to 12%, 5 to 12%, or even 5 to 10%.

A plasticizer/solubility enhancer can be, for example, an alcohol, a glycol, such as polyethylene glycol and polypropylene glycol, a non-liquid or liquid fat or oil, a liquid or non-liquid paraffin, or a combination of at least two thereof.

In one embodiment, at least one plasticizer/solubility enhancer is polyethylene glycol (PEG), cocoa butter, or a mixture thereof, preferably PEG. In some compositions, the PEG plays a role as binder and/or plasticizer.

In at least some embodiments, the PEG has a moderate to low effect, or no effect, on extrusion and on the physical aspect of the chews.

The PEG is preferably added in solid form, for example, a powder. The PEG can be solid at room temperature, but could melt at least partially during manufacturing, so as to provide additional cohesive power during compression of a mixture of powdered ingredients, along with, before or after addition of liquids.

In some embodiments, at least one plasticizer and/or binder is added in flowable or liquid form, or has a flowable or liquid form at least one time during the manufacturing of the chewable composition.

Flowable Ingredients

In one aspect of the present invention, the flowable ingredients, which may be liquids, play an important role in the final consistency of the product. In particular, the flowable ingredients and/or liquids assist in the combination of the solid ingredients to form the final product, for example, when the product is obtained by compression and/or extrusion.

A combination of wetting agent(s) and non-miscible liquid oil(s) is preferred. The wetting agent alone such as glycerin, PPG or a mixture thereof, allows for extrusion, although there is a risk of fraying and tearing of chews, at least in some instances. The liquid oil(s) can play a role as lubricant, by coating the surface of the blend during extrusion, then is re-absorbed within the product. Conversely, extrusion is often difficult or impossible when liquid oil, such as soybean oil, is used alone.

The flowable component can be added in any amounts and any order. Liquids can be mixed directly into dry ingredients or pre-mixed with each other before addition to other ingredients.

The nature of the flowable ingredient(s), and the amounts and/or order of incorporation of the flowable ingredients can be important for successful extrusion. For example, a blend that contains too much flowable ingredients is more likely to be too soft to pass through the cutter system. A blend that contains too little flowable ingredients will likely not bind together or have adequate lubrication to cleanly exit the die. Quantities, flowable ingredients ratios vary with formulation items and quantities.

In a preferred embodiment, the ratio of flowable ingredients to solid ingredients is about 15 to about 35%, preferably at least 18, more preferably at least 20%, and preferably at most 25%, more preferably 20 to 30% or even 20 to 25%, even more preferably 20 to 22%, alternatively 22 to 24% flowable ingredients.

A ratio of flowable or liquid oil to wetting agent is typically about 20 to about 60%, preferably at least 25%, more preferably at least 30%, even more preferably at least 35%, and preferably at most 55%, more preferably 50%, even more preferably at most 45%. For example, approximately 40% is flowable or liquid oil (such as soybean oil) and 60% is wetting agent (such as glycerin). Thus, the relative amount of the flowable or liquid oil is from 20 parts to 60 parts for 100 parts (w/w) of the flowable or liquid oil and glycerin.

In one aspect of the invention, the wetting agent and flowable oil are not miscible. For example, in a particular embodiment, glycerin and soybean oil are not miscible. In that case, especially when there is no, or no substantial amount of, emulsifier, the ingredients or a mixture thereof are preferably blended continuously into a slurry or slurry-like consistency, for example, as it is transferred to the dry blend for compression and/or extrusion to obtain the final product.

In at least some embodiments, slight changes to the wetting agent/lubricant ratio are critical to the disintegration profile for the chews. Thus, for example, the ratio will typically be selected differently for soft chews and for more tablet-like chews.

Regarding the addition of oil/glycerin and mixing with solid ingredients, in some embodiments, if the addition takes place separately, the mixture is not extrudable, as a dry powder mix. When adding both oil and glycerin together, an extrudable slurry is obtained in some cases.

The addition of the flowable and/or liquid ingredients at the end of mixing is preferred in some cases, as it makes these ingredients more readily available to behave as a lubricant for the extrusion process. Advantageously, a flowable or liquid oil acts as a solvent or coating only for the API(s), and the remaining dry ingredients are added afterwards.

Wetting Agents

Wetting agents that may be useful in the present invention include ethylene glycol (EG), polyethylene glycol (PEG), propylene glycol (PG), polypropylene glycol (PPG), and combinations of at least two thereof, or of at least one thereof, along with an auxiliary wetting agent(s).

The wetting ability of glycerin is useful, especially where glycerin acts as a binder to allow for easy extrusion. Glycerin wets and allows particles to bind together where the extruder compresses the blend and extrudes chews as solid units. The wetting agent, such as glycerin, is present in an amount of 10 to 20%, for example, 12 to 15%.

Alternate or additional ingredients that act as wetting agent may include the following: Propylene glycol; liquid polyethylene glycol; fatty acid esters; sorbitol, and combinations or mixtures thereof.

Non-Miscible Flowable Oils

The flowable or liquid oil(s) can be a vegetable oil or a mineral oil. Soybean oil is useful to manufacture chews by extrusion. Soybean oil typically acts as a liquid lubricant that when uniformly added to the final blend allows for clean extrusion of the dosage edges and ease of handling when cutting and packaging. Alternate or additional ingredients may include: PEG; glyceryl oleate; medium-chain triglycerides; corn oil; hydrogenated coconut and palm kernel oils; or chemically modified oils such as Mygliol® (SASOL); vegetable shortening; castor oil; mineral oils; fish oils; various esters; other vegetable oils.

The flowable or liquid oil(s) such as soybean oil can play a role as a lubricant that is often particularly useful for blend mixing, compression and/or extrusion. While mixing and extrusion may be possible without liquid oil, when flowable or liquid oil is insufficiently present, the chew appearance can be unpleasant and weight variation may be high due to the excessive fraying.

Flowable oil means that the oil is liquid, or at least flowable, e.g., pourable, at room temperature, about 20, 25, or 30° C., for example (or about 68, 77, or 86° C.).

The oil also helps to improve the smoothness and appearance of the product when it is obtained by extrusion.

Others

The composition may include a preservative or a combination of preservatives. Other additives may also be present, for example, antioxidant, coloring agent, and/or taste enhancer such as salt.

A lubricant may also be present, such as magnesium stearate or stearic acid. Various other ingredients may also be added depending on the objectives and requirements of specific embodiments, in accordance with the knowledge in the art.

Manufacturing Process

The product may be obtained by compression molding and/or extrusion, for example.

Extrusion is designed to manufacture chews of uniform weight, shape, and/or consistency. In particular, extrusion speed and/or temperature are adjusted in accordance with the desired product type, shape, size and/or other objectives.

In some embodiments of the extrusion mixture, if the speed is too low, friction of the blend against the die can cause frayed edges, and if the speed is too high, the cutter wheel signal could go beyond its limits, causing varied chew lengths and inconsistent weights.

Extrusion temperature typically plays a role in chew consistency. For example, the temperature of the extruder die can be set in the range from 80 to 150° F., or in some embodiments, 90 to 125° F. Conversely, if the extruder die is set at a high temperature, for example, significantly higher than 160° F., the blend might become too fluid, and it might not flow from the die properly in some cases.

Without being limited to a particular theory or technical reasoning, it is believed that a reason for the successful extrusion at low temperature is that, during the extrusion process, at least in some cases, the pressure of extrusion causes the liquids (or flowable ingredients) to concentrate on the surfaces, lubricating the die and reducing friction. Once cut and allowed to rest, the liquids are re-absorbed into the chew, returning the soft and moist aspect of the chews.

Thus, in some embodiments, little or no heat is applied and extrusion occurs at an applied temperature in the range from 75 to 115° F., for example. The temperature of the material during extrusion can also be adjusted as a function of the extrusion rate, so as to obtain the desired consistency of the final product without overheating the blend.

EXAMPLES

Example 1

Disintegrant

In order to study the effect of croscarmellose sodium content, development batches were made with varying quantities of the disintegrant. Disintegration comparisons were performed on medium tablets and blocks (containing either 10% or 15% croscarmellose sodium), for both Praziquantel and Ivermectin.

The disintegration results of the 15% croscarmellose sodium formula performed closer to that of the tablet of example 7 than the 10% croscarmellose sodium formula.

Disintegration profiles were then performed on tablets and the optimized blocks, and the results also showed that the 15% croscarmellose sodium formula performed closely to that of the tablet with 1% croscarmellose sodium.

Disintegration times according to USP <701> were as follows (size in inches):
Large (⅝"×⅝"×1.70"): 58 min 5 sec
Medium (½"×½"×1.33"): 44 min 21 sec
Small (7/16"×7/16"×0.80"): 31 min 55 sec
Toy (⅜"×⅜"×0.66"): 21 min 55 sec In contrast, experimental batches were made, which contained 1, 2, 5% croscarmellose sodium, respectively. These batches resulted in dissimilar disintegration profiles.

Example 2

Flowable Ingredients

This experiment studied the importance of certain ingredients within the standard soft chew formulation and the role they play in blending and extrusion of chews. The ingredients to be studied were: polyethylene glycol (PEG), soybean oil; and glycerin. PEG may be considered a flowable ingredients, or comparable to a flowable ingredients, for example, in cases where the PEG is added as a flowable ingredient, or made flowable during at least one step of the chew manufacturing process, such as extrusion or heating.

The experimental design included processing of three batches of 15 kg size blends in the Hobart HL600 planetary mixer, extrusion using the 4" twin packer Bonnot extruder, cutting with the Goodman cutter, and using the "medium" size extrusion die. One batch had reduced PEG, another batch had reduced soybean oil, and a third batch had reduced glycerin.

Soft Chew Formulations:

| Material Description | Batch 1 Reduced PEG | Batch 2 Reduced Oil | Batch 3 Reduced Glycerin |
|---|---|---|---|
| | Percentage of Formulation | | |
| Bacon Flavor | 18.0 | 18.0 | 18.0 |
| Potassium Sorbate | 0.1 | 0.1 | 0.1 |
| Sucrose | 13.0 | 13.0 | 13.0 |
| Corn Starch | 26.11 | 18.61 | 19.14 |
| Croscarmellose Sodium | 15.0 | 15.0 | 15.0 |
| Praziquantel Granulation | 4.16 | 4.16 | 4.16 |
| Polyethylene Glycol | — | 9.0 | 9.0 |
| Soybean Oil | 10.0 | 1.0 | 20.08 |
| Glycerin | 13.41 | 20.91 | 1.3 |
| TOTAL | 100.0% | 100.0% | 100.0% |

Blending/Final Blend:
Batch 1 (No PEG)
There was no observed difference from the standard formulation used in the batches.
Batch 2 (Reduced Oil)
This batch seems to stress the Hobart mixer more than the standard blend. Most of the material stuck/hung onto the paddle and wasn't adequately mixing for the last 5 of 20 minutes. The final blend appears thicker, more gum-like the previous batches.
Batch 3 (Reduced Glycerin)
This final blend has a dry appearance as compared to the previous two batches. The final blend can be described as "wet sand" and does not have a typical dough consistency.
Extrusion/Cutting:
Extrusion was performed with medium die size, at a temperature of 85° F. except indicated otherwise, jacket temperature of 55° F., for a chew weight of 3.3-3.6 g.

Batch 1 (No PEG)
This batch extruded similar to tablet chews but without the PEG particles. There was some excessive oil and frayed edges.
Batch 2 (Reduced Oil)
This blend extruded but the extrudate was frayed, no smooth surfaces on the chews.
Batch 3 (reduced glycerin)
This blend did not extrude. The few chews that eventually pushed through the cutter were dry and crumbly. Excessive oil seeped from the extruder, more oil observed than any previous soft chew batch.

Conclusion: this example underlines the criticality of minimal effective amounts of flowable ingredients, e.g., liquids, especially wetting agent(s) and/or flowable oil(s).

Example 3

Liquid Mixing

In the following experiment, the order of liquid addition was modified to remove the premixing of immiscible liquids. Visible observations were made on blends and chews.

| Order of Addition | Batch purpose/Observations/Notes |
|---|---|
| Liquid premix. | Powder to replace granulated sugar. Normal blend/chews. |
| Glycerin then oil. | Placebo. Normal blend/chews. |
| Glycerin then oil. | Cocoa butter replacing PEG. Normal blend/chews. |
| Glycerin then oil. | Labrafac Lipophile replacing PEG. Normal blend/chews. |
| Glycerin then Labrafil | Labrafil (apricot kernel oil) replacing soybean oil. Normal blend/chews. |
| Propylene glycol then oil | Propylene glycol replacing glycerin. Normal blend/chews. |

As shown in the example above, a preliminary mixing of the liquids results in normal blend and/or chews, as well as adding the oil or oil substitute after the glycerin or analog (propylene glycol). In particular, adding glycerin to the blend followed by soybean oil seemed to produce final blends and extruded chews that are similar to premixing oil and glycerin together. In some cases, adding oil first seemed to cause smearing and sticking within the Hobart mixer.

Example 4

Extrudable Blend

An extrudable blend was prepared in accordance with the present description.

| | Formula Final Blend | | |
|---|---|---|---|
| | Ingredient | Function | Quantity (%) |
| Mixing Step 1 | Bacon Flavor | Flavor | 18.000% |
| | Croscarmellose Sodium | Disintegrant | 15.000% |
| | Sucrose | Filler/Sweetener | 13.000% |
| | Polyethylene Glycol | Binder | 9.000% |
| | Corn Starch | Filler/Disintegrant | 8.150% |
| | Pyrantel Pamoate Granulation | Active | 6.540% |
| | Praziquantel Granulation | Active | 3.760% |
| | Ivermectin Granulation | Active | 2.030% |
| | Potassium Sorbate | Preservative | 0.100% |

-continued

| | Formula Final Blend | | |
|---|---|---|---|
| | Ingredient | Function | Quantity (%) |
| Mixing Step 2 | Magnesium Stearate | Lubricant | 1.000% |
| Mixing Step 3 | Glycerin | Lubricant/Softener | 13.410% |
| | Soybean Oil | Lubricant/Softener | 10.000% |
| | 20% Butylated Hydroxytoluene in Corn Oil | Antioxidant | 0.010% |
| | Total: | | 100.000% |

Concentration of disintegrant (croscarmellose sodium) was set to 15% in the chew as opposed to 1% in a corresponding tablet, which resulted in successfully maintaining bioequivalence with the tablet, i.e., giving the extruded chews a quicker disintegration time than with less disintegrant.

Example 5

Stability

Stability was successfully tested in stability chambers for the composition of Example 4, in toy- and large-size chews at 25° C./60% RH.

25° C./60% RH–T=0, 1, 2, 3, 6, 9, 12, 18, 24, 30 & 36-Month

40° C./75% RH–T=0, 1, 2, 3 & 6-Month

30° C./65% RH samples were kept, but not tested in the absence of a failure with the 40° C./75% RH samples.

Small and medium chews were also placed in the stability chambers, but tested only if the toy or large chews had stability failures.

Comparative Example 6

Disintegration

The objective was to compare the disintegration of various comparative starch-based chews (typically more than 25-30%) with soft chew samples according to the invention.

A disintegration study was performed by simply placing one chew of each type into 4 oz sample jars containing approximately 80 grains of deionized water and make observations over time. Observations of the chews were made over a 6 day period and are outlined in the table below. The following chews were studied:

| Date/Time | Heartgard (dogs up to 25#) | Sentinel Spectrum (dogs 8.1-25#) | Nexgard (dogs 10.1-24.0#) | Product according to the invention (small 1.5 g) |
|---|---|---|---|---|
| After 25 min | No Change | Color fade | Some disintegration | Moderate disintegration |
| After 1 day | Little change | Swollen with cracks | Disintegrated | Disintegrated |
| After 2 days | Little change, water color change | Swollen with crumbles. | Disintegrated | Disintegrated |
| After 3 days | Little change | Crumbled | Disintegrated | Disintegrated |
| After 6 days | Rectangle shape still intact, water turned black | Crumbled to disintegration | Disintegrated | Disintegrated |

All chews tested in this study disintegrated in deionized water in a timely fashion except for Heartgard which exhibited almost no signs of swelling or disintegration. Also, Heartgard was the only sample that appeared to show microbial growth under these conditions. The product according to the invention disintegrated within minutes.

Comparative Example 7

| Formula for final blend, tablet form | |
|---|---|
| 7.6% | Microcrystalline cellulose |
| 1.0% | Croscarmellose sodium |
| 5.5% | Sugar |
| 2.0% | Silicon dioxide |
| 19.0% | Flavor |
| 62.9% | Actives |
| 2.0% | Magnesium stearate |

The microcrystalline cellulose, croscarmellose sodium, and sugar are screened separately and blended. The silicon dioxide and flavor are screened and blended. A blender is charged with the microcrystalline cellulose/croscarmellose sodium/sugar mixture and mixed for 10 minutes. The blender is charged with the actives in granulated form that have been pre-screened. The pre-screened magnesium stearate is manually blended with a portion of the blended product from the blender, then the material is blended in the blender. The final blend is discharged into pressed into tablets so as to meet tablet hardness, weight, and appearance requirements.

CLOSURE

Particular embodiments and examples described herein are illustrative only and are not intended to limit the scope of the present invention. The person skilled in the art will recognize that embodiments of the present invention can include features from several of the above embodiments and examples.

The invention claimed is:

1. An extruded chewable composition, comprising, in percentages by weight of a total weight of the composition (w/w):
   at least one pharmaceutically active ingredient component;
   solid components including:
   at least one flavor including more than 10% (w/w) of a meat flavor; and at least one disintegrant including at least 10% (w/w) of at least one non-starch disintegrant, and flowable components including:

from 5% to 15% (w/w) of a flowable oil; and from 10% to 20% (w/w) of glycerin, wherein a relative amount of the flowable oil is from 20 parts to 60 parts for 100 parts (w/w) of the flowable oil and glycerin, wherein the composition contains less than 2% (w/w) unbound water.

2. The chewable composition of claim 1, wherein the flavor includes from 15% to 25% (w/w) of the meat flavor.

3. The chewable composition of claim 1, wherein the meat flavor includes a meat powder.

4. The chewable composition of claim 1, wherein the flavor includes a sweet flavor.

5. The chewable composition of claim 1, wherein the non-starch disintegrant is croscarmellose sodium.

6. The chewable composition of claim 1, wherein the flowable oil is a liquid oil.

7. The chewable composition of claim 1, wherein the flowable oil is a vegetable oil.

8. The chewable composition of claim 1, wherein the flowable oil is soybean oil.

9. The chewable composition of claim 1, comprising:

at least 25% (w/w) of the flavor; and at least 15% (w/w) of the disintegrant.

10. The chewable composition of claim 9, wherein the flavor includes at least 12% (w/w) of the meat flavor.

11. The chewable composition of claim 9, wherein the flavor includes at least 10% (w/w) of a sweet flavor.

12. The chewable composition of claim 1, comprising:

at least 12% (w/w) of the meat flavor; and from 10% to 20% (w/w) of the non-starch disintegrant.

13. The chewable composition of claim 12, comprising:

from 15% to 25% (w/w) of the meat flavor.

14. The chewable composition of claim 13, comprising from 5% to 15% (w/w) of polyethylene glycol.

15. The chewable composition of claim 13, comprising from 5% to 15% (w/w) of a sweet flavor.

16. The chewable composition of claim 13, comprising from 2% to 12% (w/w) of starch-based filler.

17. The chewable composition of claim 13, wherein the amount of glycerin and the flowable oil is from 20% to 30% (w/w).

18. The chewable composition of claim 13, which contains less than 5% (w/w) of cellulose-, soy- and silicone-based fillers.

19. The chewable composition of claim 1, comprising from 12 to 25% (w/w) of a meat flavor and from 10 to 23% (w/w) of a sweet flavor.

20. The chewable composition of claim 1, comprising up to 12% (w/w) of starch.

21. The chewable composition of claim 1, comprising from 5% to 15% (w/w) of polyethylene glycol.

22. An extruded chewable composition, comprising, in percentages by weight of a total weight of the composition (w/w):

from 0.01% to 10% (w/w) of at least one pharmaceutically active ingredient;

from 25 to 35% (w/w) of a flavor including from 12 to 25% (w/w) of a meat flavor and from 10 to 23% (w/w) of a sweet flavor;

from 5 to 12% (w/w) of polyethylene glycol, cocoa butter, or a mixture thererof;

from 10 to 20% (w/w) of a non-starch disintegrant;

from 5 to 12% (w/w) of a starch;

from 12 to 15% (w/w) of glycerin; and from 8 to 12% (w/w) of a liquid oil, wherein a relative amount of the liquid oil is from 20 parts to 60 parts for 100 parts (w/w) of the liquid oil and glycerin, wherein the composition contains less than 2% (w/w) unbound water.

23. The chewable composition of claim 22, comprising from 5% to 10% (w/w) of starch.

24. The chewable composition of claim 22, comprising from 5% to 8% (w/w) of starch-based filler.

25. The chewable composition of claim 22, comprising from 5% to 12% (w/w) of polyethylene glycol.

* * * * *